(12) United States Patent
Hösel

(10) Patent No.: US 6,452,157 B1
(45) Date of Patent: Sep. 17, 2002

(54) APPARATUS INTEGRATED IN A FIBER PROCESSING MACHINE FOR RECOGNIZING AND PROCESSING IMPURITIES

(75) Inventor: Fritz Hösel, Mönchengladbach (DE)

(73) Assignee: Trützschler GmbH & Co. KG, Mönchengladbach (DE)

( * ) Notice: Subject to any disclaimer, the term of this patent is extended or adjusted under 35 U.S.C. 154(b) by 109 days.

(21) Appl. No.: 09/714,831

(22) Filed: Nov. 17, 2000

(30) Foreign Application Priority Data

Nov. 17, 1999 (DE) .......................... 199 55 292

(51) Int. Cl.[7] .............................. G01J 1/04; G01J 1/42; G01J 5/08
(52) U.S. Cl. ............................ 250/227.14; 250/227.15; 250/227.16
(58) Field of Search ..................... 250/227.14, 227.15, 250/227.16, 227.11, 227.17, 227.27, 226, 559.27

(56) References Cited

U.S. PATENT DOCUMENTS 6,333,510 B1 * 12/2001 Watanabe et al. ...... 250/559.27

FOREIGN PATENT DOCUMENTS

| DE | 24 53 028 | 6/1975 |
| DE | 31 47 113 | 6/1983 |
| DE | 297 19 245 | 4/1998 |
| EP | 0 399 945 | 11/1990 |
| EP | 0 545 129 | 6/1993 |
| EP | 0 652 432 | 5/1995 |
| GB | 2 166 865 | 5/1986 |

* cited by examiner

*Primary Examiner*—Hung Xuan Dang
(74) *Attorney, Agent, or Firm*—Venable; Gabor J. Kelemen

(57) ABSTRACT

An apparatus for detecting foreign bodies in fiber material includes at least two light sources. At least one of the light sources has at least three light emitting elements. Each light emitting element radiates a light of different color. An arrangement directs the light emitted by the light sources to the fiber material for illuminating the fiber material, and a sensor detects the illuminating light after illumination of the fiber material for emitting an electric signal upon a sudden color change of the fiber material. An arrangement causes the light sources to alternatingly illuminate the fiber material with different colors, and further, an arrangement selects the color emitted by the light sources as a function of the color of the fiber material.

20 Claims, 3 Drawing Sheets

APPARATUS INTEGRATED IN A FIBER PROCESSING MACHINE FOR RECOGNIZING AND PROCESSING IMPURITIES

CROSS REFERENCE TO RELATED APPLICATION

This application claims the priority of German Application No. 199 55 292.4 filed Nov. 17, 1999, which is incorporated herein by reference.

BACKGROUND OF THE INVENTION

This invention relates to an apparatus integrated in a fiber processing machine, such as a spinning preparation machine or a spinning preparation line for recognizing and processing impurities, foreign bodies and foreign fibers in textile fiber material. The apparatus has at least two light sources which illuminate the fiber material alternatingly with different colors and further, a sensor is provided which detects the colors of the light after it impinges on the fiber material. An electric signal is generated if an abrupt color change of the fiber material from a predetermined color occurs.

European Patent 0 399 945 discloses an apparatus in which one or several two-color (red and green) LED light sources are provided for alternatingly emitting red and green (thus, narrow-band) light. It is a disadvantage of this prior art arrangement that the colors may not be adapted to the prevailing needs, since only red and green lights are alternatingly emitted. It is a particular drawback that with one light diode neither a light of another color, for example, white, yellow or blue color nor a color mixture may be generated and emitted.

SUMMARY OF THE INVENTION

It is an object of the invention to provide an improved apparatus of the above-outlined type from which the discussed disadvantages are eliminated and which, in particular, adapts the light colors to the application at hand, for example, to different or varying colors of the fiber material.

This object and others to become apparent as the specification progresses, are accomplished by the invention, according to which, briefly stated, the apparatus for detecting foreign bodies in fiber material includes at least two light sources. At least one of the light sources has at least three light emitting elements. Each light emitting element radiates a light of different color. An arrangement directs the light emitted by the light sources to the fiber material for illuminating the fiber material, and a sensor detects the illuminating light after illumination of the fiber material for emitting an electric signal upon a sudden color change of the fiber material. An arrangement causes the light sources to alternatingly illuminate the fiber material with different colors, and further, an arrangement selects the color emitted by the light sources as a function of the color of the fiber material.

The multi-colored light source, particularly a multi-colored light diode, provides that by means of a single structural element the generation and emission of a plurality of colors with a minimum spatial requirement may be achieved. The universal light color generation may be effected by means of a simple electric control circuit. By selecting a color or colors from a large spectrum, an illumination with an individual, application-specific light color is possible.

The invention has the following additional advantageous features:

The colors are variable.

The multi-colored light source is connected to a control device which determines the particular color or color combination with which the multi-colored light source illuminates.

The multi-colored light source may illuminate simultaneously with more than one color.

The multi-colored light source may illuminate alternatingly with more than one color.

The multi-colored light source is a multi-colored light diode.

The multi-colored light source may produce light in a large frequency range.

Light flashes of different color may be generated sequentially and at short intervals.

The sensor is a camera which produces an image for each individual light flash.

Particular colors emitted by the light source may be selected for the light flash as a function of the fiber material to be examined.

The colors with which the light source illuminates are individually determinable.

The light source may be used essentially with a single color (standard color) and, dependent on image evaluation, with at least one further color.

The standard color may be set manually based on an optical impression or it may be set automatically, for example, by means of a color measuring sensor which is coupled electrically with the image processing system, for example, by means of a data interface.

The standard color may be set continuously based on the measuring magnitude of the color measuring sensor.

The color measuring sensor is associated with a fiber processing machine, such as a bale opener.

A position measuring device for the tuft removing mechanism of the bale opener is coupled to the image processing system.

A multi-colored light source is utilized.

At least one multi-colored illuminating element (diode) is coupled to an electronic image data processing device.

The multi-colored illuminating system may emit light of different colors as a function of control.

The color or colors of the multi-colored light source are variable.

DESCRIPTION OF THE PREFERRED EMBODIMENT

Figure 1:
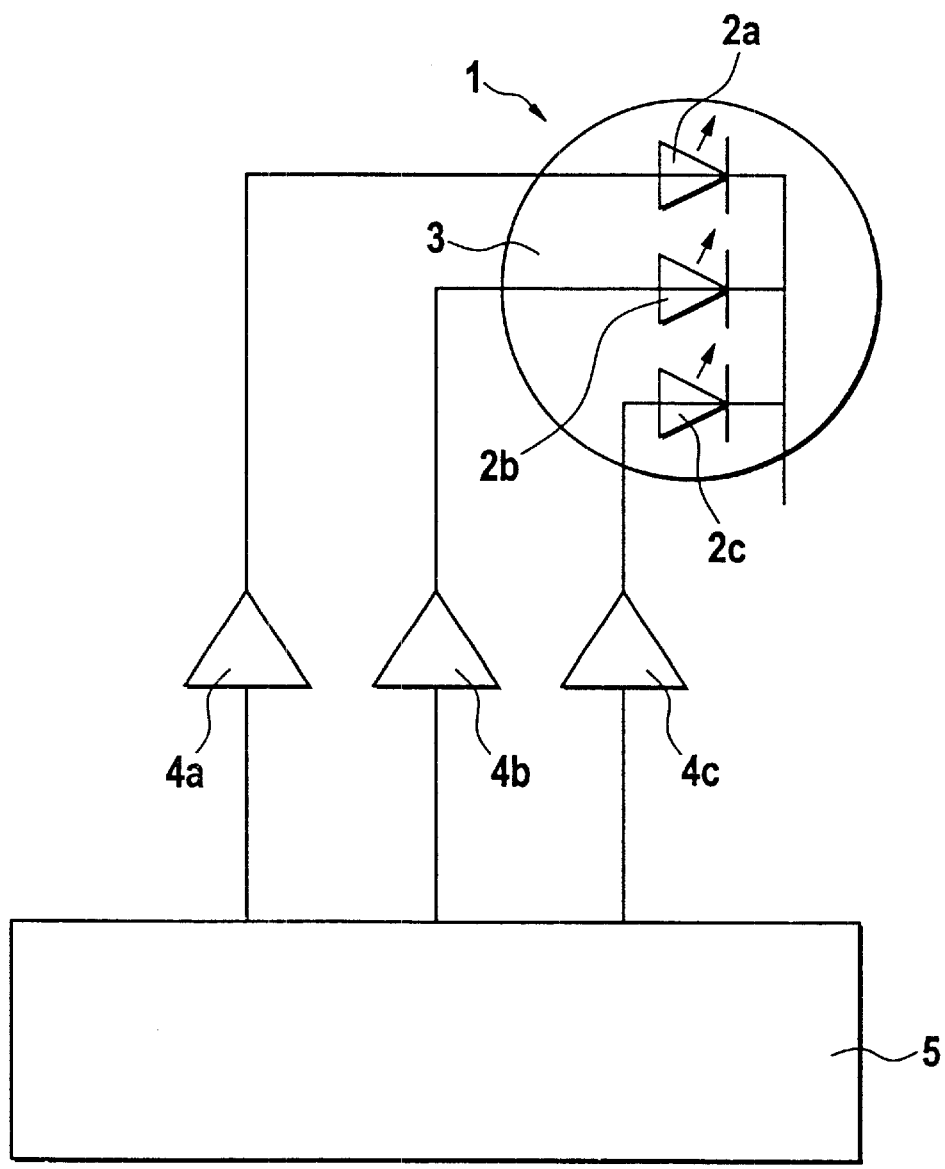
FIG. 1 is a block diagram illustrating a three-colored illuminating element (diode) coupled to a control apparatus.

FIG. 1 shows a multi-colored light source 1 having three light diodes 2a, 2b and 2c which emit light of three different colors, such as red, blue and green, respectively, and which are accommodated in a housing 3 made of a transparent synthetic material. The arrows show the direction of the emitted light. The light diodes 2a, 2b and 2c are coupled to a control device 5 such as a microprocessor via respective amplifiers 4a, 4b and 4c. By means of the red-green-blue light diode 1, all colors of the visible spectrum may be generated.

The different colors are produced by setting the light intensity for the individual diodes 2a, 2b and 2c by the control apparatus 5. The light intensity is determined predominantly by the current flowing through the diodes.

The control apparatus 5 and the amplifiers 4a, 4b, 4c accurately control the currents which flow through the individual diodes and thus the desired color may be set. Instead of the amplifiers 4a, 4b and 4c, other controllable current sources may be used as well.

Figure 2:
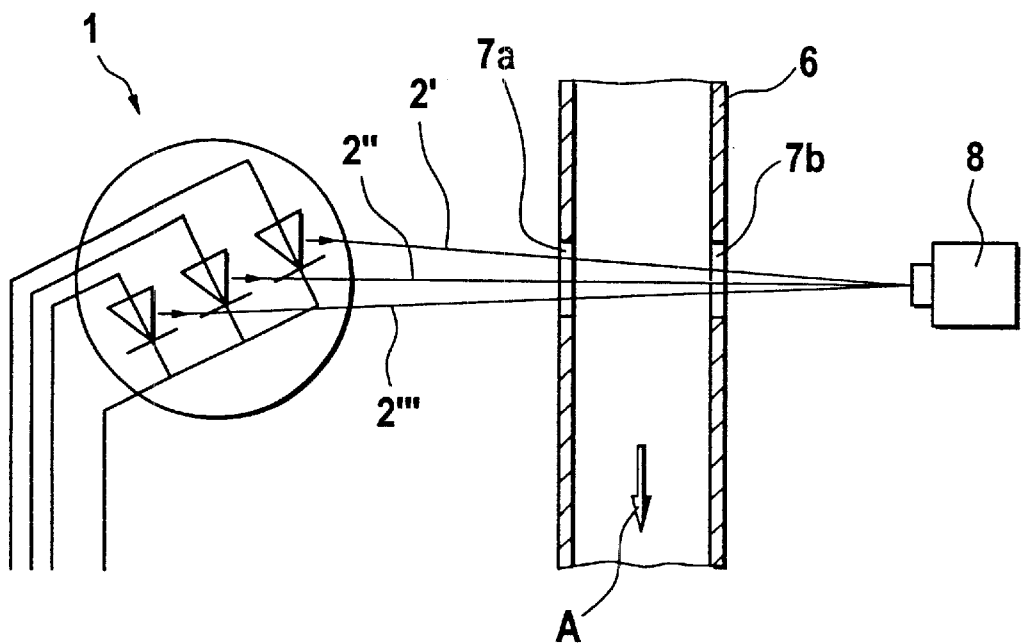
FIG. 2 shows a tubular conduit for pneumatically transporting fiber tufts, as well as the three-colored illuminating element of FIG. 1 and a sensor camera disposed in alignment at opposite sides of the tubular conduit.

The fiber tufts A such as cotton fiber tufts are pneumatically transported in the conduit 6, as shown in FIG. 2. In the wall of the conduit 6 whose cross section may be rectangular, quadratic or circular, two facing windows 7a and 7b of a transparent material (such as glass or plexiglas) are formed. The three-colored illuminating element 1 and a camera 8 are positioned on opposite sides of the conduit 6 externally thereof and are in alignment with a respective window 7a, 7b. The light beams 2', 2" and 2'" are essentially parallel between the light diodes 2a, 2b and 2c and the inner wall of the housing 3. The curved shape of the housing 3 causes the light beams 2', 2", 2'" to converge in the direction of the conduit 6 and the camera 8. Within the conduit 6 the light beams 2', 2", 2'" form light spots traversed by the fiber material formed preferably of fiber tufts of approximately 10 mm in diameter. The light beams 2', 2" and 2'" thereafter impinge on the camera 8 (sensor) which is preferably a CCD camera.

Figure 3:
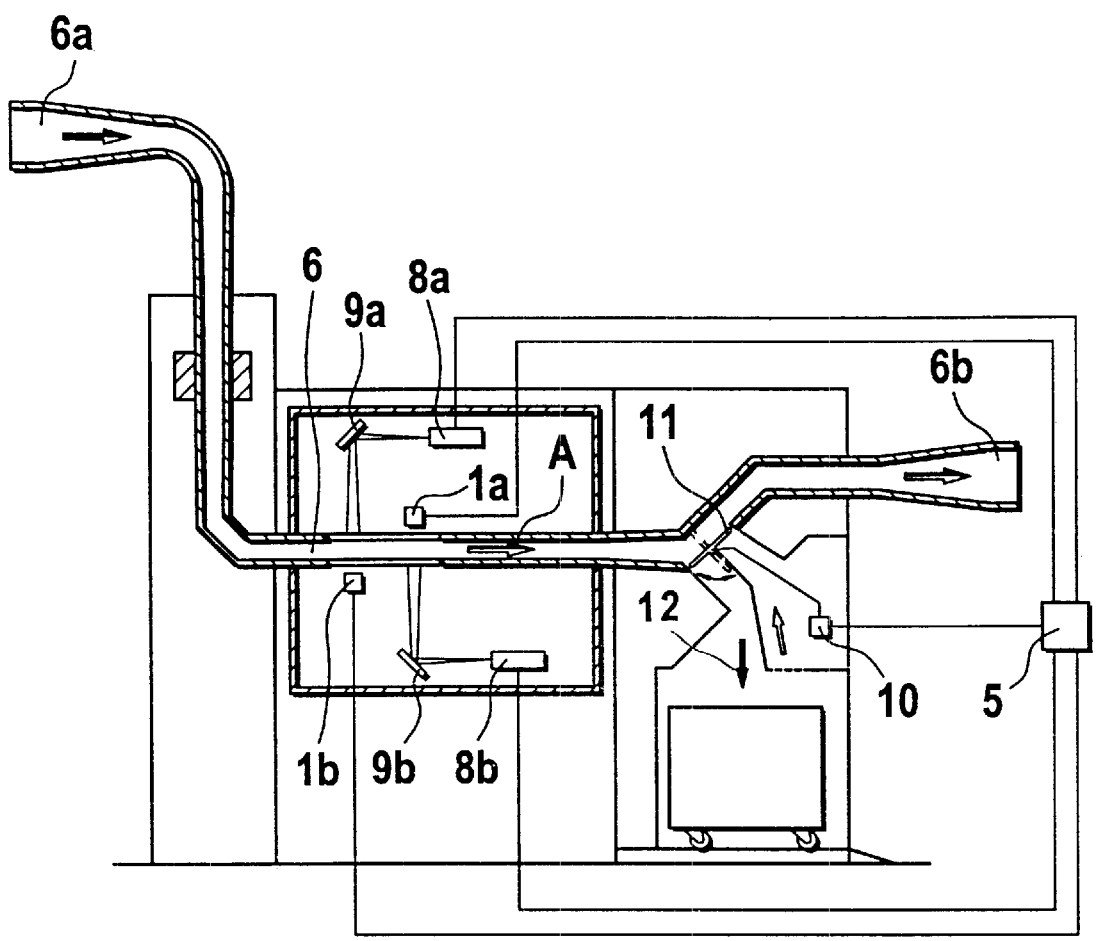
FIG. 3 is a schematic side elevational view of an apparatus for separating foreign bodies from a pneumatically conveyed fiber tuft stream, incorporating the apparatus according to the invention.

Turning to FIG. 3, two devices according to the invention are integrated in a foreign body separator of the model SECUROMAT SC manufactured by Trützschler GmbH & Co. KG, Mönchengladbach, Germany. On opposite sides of the conduit 6 respective multi-colored light sources 1a, 1b are provided which are aligned with respective deflecting mirrors 9a and 9b disposed on the other side of the conduit 6. The mirrors, in turn, direct the light into respective cameras 8a, 8b. The multi-colored light sources 1a, 1b as well as the cameras 8a, 8b are connected to the electronic control device 5 which controls an ejector flap 11 via a flap operator 10. The flap 11 has, as controlled by the apparatus 5, a normal position (shown in solid lines) to direct the fiber material into the conduit outlet 6b and an ejecting position (shown in phantom lines) to momentarily direct fiber material with the detected foreign bodies, foreign fibers and the like into the waste space 12. The input 6a of the conduit 6 may be connected, for example, to an automatic bale opener which may be a BLENDOMAT BDT model while the outlet 6b of the conduit 6 may be connected, for example, to a multi-mixer MSM 6 model which, in turn, inputs the material to a cleaner which may be a CLEANOMAT CVT 4 model; all three identified models are manufactured by Trützschler GmbH & Co. KG.

It will be understood that the above description of the present invention is susceptible to various modifications, changes and adaptations, and the same are intended to be comprehended within the meaning and range of equivalents of the appended claims.

What is claimed is:

1. An apparatus for detecting foreign bodies in fiber material, comprising (a) at least two light sources; at least one of said light sources being a multi-colored light source including at least three light emitting elements, each light emitting element emitting a light of different color;

(c) means for directing the light emitted by the light sources to the fiber material for illuminating the fiber material;

(d) a sensor detecting the illuminating light after illumination of the fiber material for emitting an electric signal upon a sudden color change of the fiber material;

(e) means for causing said light sources to alternatingly illuminate the fiber material with different colors; and (f) means for selecting the color emitted by said multi-colored light source as a function of the color of the fiber material.

2. The apparatus as defined in claim 1, wherein said multi-colored light source is a multi-colored light diode.

3. The apparatus as defined in claim 1, wherein said sensor comprises a camera.

4. The apparatus as defined in claim 1, further comprising an electronic image processing device connected to said at least one multi-colored light source.

5. The apparatus as defined in claim 1, further comprising a color sensor for determining a standard color to be emitted by at least one of said light sources as a function of the color of the fiber material.

6. The apparatus as defined in claim 5, in combination with a bale opener; said bale opener having a tuft removing mechanism; said color sensor being connected to said tuft removing mechanism.

7. The apparatus as defined in claim 1, further comprising a control device; said at least one multi-colored light source being connected to said control device.

8. The apparatus as defined in claim 7, wherein said control apparatus comprises means for determining the color with which said multi-colored light source illuminates the fiber material.

9. The apparatus as defined in claim 7, further comprising a color sensor for determining a standard color to be emitted by at least one of said light sources as a function of the color of the fiber material; said color sensor being connected to said control device.

10. The apparatus as defined in claim 7, further comprising a foreign body ejecting device connected to and controlled by said control device.

11. The apparatus as defined in claim 7, wherein said sensor comprises a camera connected to said control device.

12. The apparatus as defined in claim 11, wherein said camera is a CCD camera.

13. The apparatus as defined in claim 1, further comprising a control device for varying the colors.

14. The apparatus as defined in claim 1, wherein at least two of said light sources are multi-colored light sources.

15. The apparatus as defined in claim 1, further comprising a control device for generating light flashes with different colors in a rapid sequence.

16. The apparatus as defined in claim 1, further comprising a control device for generating intermediate colors with said multi-colored light source.

17. The apparatus as defined in claim 1, further comprising a control device for generating a single color with said multi-colored light source.

18. The apparatus as defined in claim 1, further comprising a control device for generating different colors in an alternating sequence with said multi-colored light source.

19. The apparatus as defined in claim 1, further comprising a control device for selecting a color for light flashes as a function of the fiber material.

20. The apparatus as defined in claim 1, further comprising a control device for generating light with said multi-colored light source in a wide frequency range.

* * * * *